United States Patent [19]

Zimble

[11] Patent Number: 4,883,425
[45] Date of Patent: Nov. 28, 1989

[54] DENTAL PROBE ASSEMBLY

[76] Inventor: Alan W. Zimble, 507 Blackgates Rd., Wilmington, Del. 19803

[21] Appl. No.: 236,773

[22] Filed: Aug. 26, 1988

[51] Int. Cl.⁴ .............................................. A61C 3/00
[52] U.S. Cl. ...................................... 433/32; 128/776
[58] Field of Search ................... 433/32; 128/774, 776

[56] References Cited

U.S. PATENT DOCUMENTS

| 4,677,756 | 7/1987 | Simon et al. | 128/776 |
| 4,764,114 | 8/1988 | Jeffcoat | 128/776 |

Primary Examiner—Robert Peshock
Attorney, Agent, or Firm—Connolly & Hutz

[57] ABSTRACT

A dental probe assembly includes a tool having a handle portion at one end thereof with a probe mounted at the other end. The probe is made of a light conducting member associated with means for transmitting light to the probe. The tool also includes means for sensing the amount of light conducted by the probe. In use the probe would be inserted into a gum pocket and by sensing the amount of light on the probe would be sensed which would correspond to the length of the probe outside of the pocket. The depth of the pocket would be determined from this value.

17 Claims, 2 Drawing Sheets

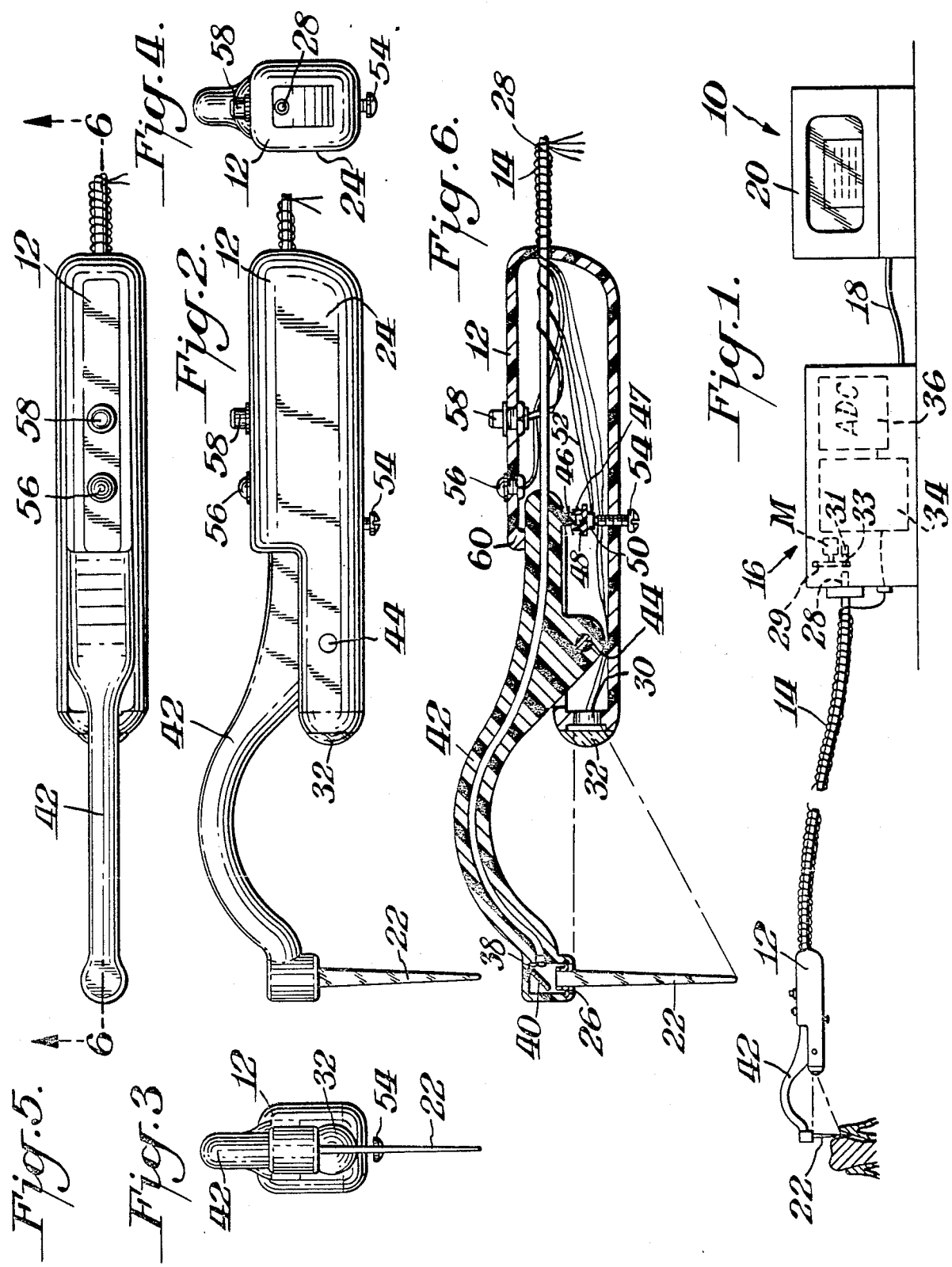

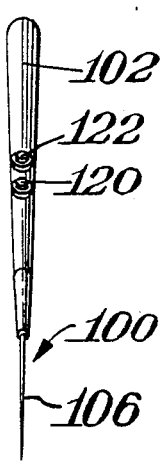
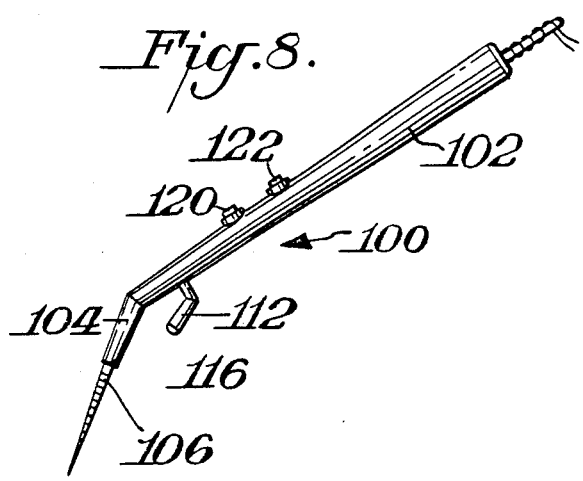
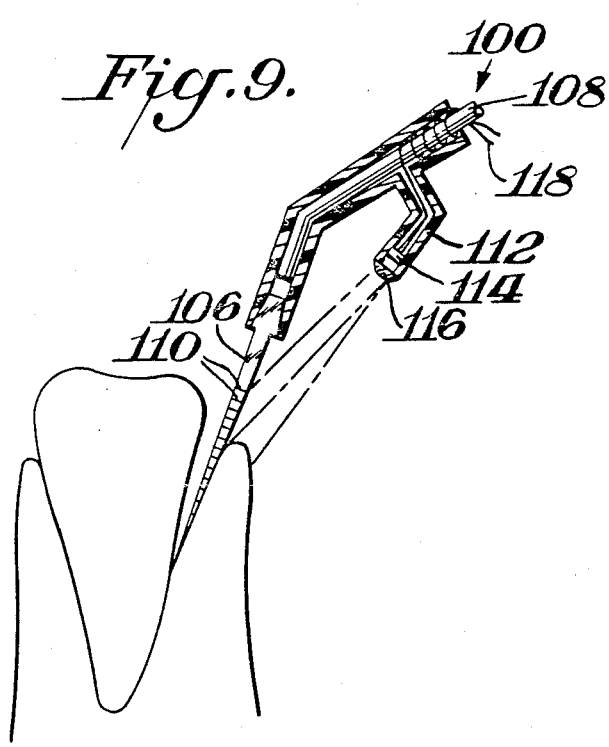

DENTAL PROBE ASSEMBLY

BACKGROUND OF THE INVENTION

Various devices exist for measuring the depth of a gum pocket in periodontal or other dental treatments. These devices generally include inserting some form of probe into the pocket and having a scale associated with the probe so as to measure the depth of the pocket. Such devices are of varying reliability because their effectiveness depends to a great extent upon requiring a uniform force from measurement to measurement in inserting the probe into the pocket where manual pressure is used to apply that force. There is a virtual certainty that uniform and reliable results will not be obtained.

SUMMARY OF THE INVENTION

An object of this invention is to provide a dental probe assembly which automatically and reliably measures the depth of a gum pocket.

A further object of this invention is to provide such a probe assembly which can result in a printed record being formed indicating the depth of the gum pocket.

In accordance with this invention the dental probe assembly is in the form of a tool having a handle at one end thereof. A probe is detachably mounted to the opposite end of the handle for insertion into the gum pocket. The probe is made of a uniform light conducting material and may be provided with a scale thereon. Light is transmitted to the probe. In use the probe is inserted into the gum pocket until the base of the pocket is reached. The tool includes sensing means having a field of view corresponding the length of the probe. The sensing means includes means for measuring the amount of light in this field of view. Accordingly, when the probe is inserted into the pocket the depth of the pocket would correspond to a length which no longer transmits light. In other words, the sensing means would only sense the amount of light corresponding to the length of the probe outside of the pocket. By comparing this amount of light with a reference which corresponds to the complete length of the probe and subtracting the reading from the reference it is possible to determine the depth of the pocket.

In a preferred form of this invention, the sensing means is associated with a printing device which automatically makes the conversion to the pocket depth and provides a written record of the pocket depth. Preferably light is transmitted to the probe by fiber optics.

THE DRAWINGS

FIG. 1 is a side elevation view of a dental assembly of this invention;

FIG. 2 is a side elevation view of a tool used in the assembly shown in FIG. 1;

FIGS. 3–4 are front and rear end elevation views of the tool shown in FIG. 2;

FIG. 5 is a top plan view of the tool shown in FIGS. 2–4;

FIG. 6 is a cross-sectional view taken through FIG. 5 along the lines 6—6;

FIG. 7 is a front elevation view of a modified form of tool in accordance with this invention;

FIG. 8 is a side elevation view of the tool shown in FIG. 7; and

FIG. 9 is a cross-sectional view in elevation showing the tool of FIGS. 7-8 in operation.

DETAILED DESCRIPTION

FIG. 1 illustrates a dental probe assembly 10 in accordance with this invention. As shown therein the assembly 10 includes a hand held portable tool 12 connected by wiring 14 and fiber optics 28 to a computer 16 which in turn is connected by a cable 18 to a printer 20. The tool itself includes a detachable, disposable probe 22 inserted into the gum pocket of a tooth as is illustrated in FIG. 1. A protective jacket may be provided over the tool leaving only the probe 22 exposed. The jacket thus would act as a sanitary barrier which could be removed and discarded after use of the tool on a patient with another jacket being applied prior to use on the next patient.

FIGS. 2-6 show in greater detail the features of the tool 12. As shown therein the tool 12 has a handle section 24 at one end thereof with the probe 22 being secured to the other end thereof. In the preferred practice of this invention probe 22 is detachably mounted in any suitable manner such as by a plastic spring gripper element 26. A significant feature of this invention is that probe 22 is made of a uniform light conducting material such as a plastic material which has light transmitted thereto in any suitable manner and preferably by fiber optics 28 so that probe 22 is illuminated.

Tool 12 also includes an optical sensing section which comprises a photodiode 30 associated with a lens 32 for creating a field of view corresponding to the general field of the length of probe 22 as indicated by the dashed lines in FIG. 6.

As shown in FIG. 1 the fiber optics 28 is connected to a light source arrangement comprising a light 31 directed against a chopper 29 having a chopper hole 33. Chopper 29 is rotated by motor M so that light is intermittently transmitted to fiber optics 28. Use of pulsating light such as from chopper 29 is advantageous sin providing uniformity in light conditions. This is accomplished by measuring the relative difference in light intensity to eliminate other variables such as from the patient's head turning or blood being on the point of the probe. Other light sources may also be used such as a standard non-pulsating light source transmitting light to fiber optics 28. Another light source enhancement could be achieved by generating a specified narrow frequency band of light to which the photo-diode is sensitized and thereby limit measurement error from ambient light.

The electrical wiring which is connected at one end to photodiode 30 and the other wiring in tool 12 becomes wiring 14 which is connected to analog process board 34. Computer 16 further includes an analog digital converter (ADC) 36 which registers a value of the amount of light sensed by photodiode 30 with a complete field of view to act as a reference value. In other words, this reference value corresponds to the amount of light sensed when viewing probe 22 before it is inserted into the gum pocket. This reference value is compared by ADC 36 to the amount of light sensed when probe 22 is in the gum pocket which would correspond to the length of the probe extending out of the pocket. By using a subtractive method it is possible therefore to determine the length of the probe 22 within the pocket which in turn would correspond to the depth of the pocket. Once this determination is made the depth can be recorded on printer 20. Accordingly, the deeper the pocket the less amount of light would be sensed by photodiode 30 which in turn would mean a greater differential when compared to the reference or standard value and that difference could be translated into a depth reading. For example, with a 15 mm long probe inserted into a pocket 7 mm deep, light would be sensed over 8 mm length of probe.

If desired probe 22 can also be provided with a scale such as in millimeters so that there would be an immediate visual reading by the dentist or hygienist, as well as or without the necessity of having a printer readout.

As shown in FIG. 6 the light transmitted from fiber optics 28 would be transmitted through lens 38 and then reflected from mirror 40 and to probe 22.

FIG. 6 also illustrates the neck portion 42 of tool 12 to be pivotally mounted at pin 44. A stop member 60 is provided in the handle portion 24 to limit the amount of pivotal movement of neck 42. Neck portion is preferably curved. Neck 42 includes a guide rod 46 around which is mounted a sleeve 47 carrying a load cell 50. Sleeve 47 is urged by coil spring 48 away from rod 46 to maintain load cell 50 in contact with threaded pressure adjusting member 54. Member 54 may be moved into or out of the handle wall to control the amount of pressure against load cell 50. Load cell 50 is electrically connected to analog process board 34 by means of wiring 52 which becomes part of wiring 14. Load cell 50 functions to activate photodiode 30 upon the reaching of a predetermined pressure slightly in excess of the pressure from member 54. Such pressure results when resistance is met by probe 22 reaching the bottom of the gum pocket to cause a slight pivotal action of neck 42 which causes load cell 50 to react against spring 48 to further press against threaded adjusting member 54. Any change in the force of spring 48 may be taken into account by suitable adjustment of member 54 to provide a proper calibration.

As shown in FIGS. 2-6 an LED 56 and a manual button 58 are provided on the top surface of handle 24. The wiring for LED 56 and button 58 becomes part of wiring 14. LED 56 lights automatically when the pressure is correct to indicate that a reading is being taken. Manual button 58 is provided to provide a calibration or reference reading of the probe when the probe is out of the gum pocket. Thus button 58 would be depressed to actuate photodiode 30 for the taking of the reference reading.

The computer may be programmed to give readings in sequence for all 32 teeth pockets, but other means are possible and not excluded. The dentist or other operator taking the depth readings would depress a button to signal the computer that a reading is being taken for the next pocket thus permitting any number of pocket readings for any tooth (usually 4 or 6 readings). For example, when a reading is taken of tooth number 1 the printout from printer 20 would identify number 1 and a depth reading such as 5 mm. If the next reading is for pocket number 2 a button on handle 24 would be depressed to signal the computer. Such button could be a separate button or could be button 58 being held depressed, instead of momentarily depressed. The printer readout would then list tooth number 2 and a depth reading. If more than one reading of tooth 2 is desired, the computer actuating button would not be depressed and the readout would still identify pocket number 2. If teeth were missing or the dentist wished to skip to a later tooth, the computer actuating button would be depressed the appropriate number of times to advance the sequence to the desired pocket without taking any intermediate readings.

In use, probe 22 would be placed in the mouth near the gum pocket, but just before probe 22 is inserted into the gum pocket, button 58 would be depressed so that a reading would be taken to provide a reference which will later be used to determine the depth of the pocket. This reference reading would indicate the value sensed for the entire length of probe 22 being illuminated under ambient conditions in the area of the gum pocket. After the reference reading is taken, probe 22 is inserted into the pocket and when the base of the pocket is reached there will be a slight pivotal movement of neck 42 to increase the pressure against load cell 50 to cause a second reading to be automatically be taken which will correspond to the length of the probe 22 still extending out of the pocket. LED 56 will light to indicate that the reading is being taken. By the subtractive light method, the length of the probe in the pocket will be calculated which will correspond to the depth of the pocket. The pocket depth will be indicated by a readout from printer 20 and will also be immediately known from a mm scale on probe 22.

Although FIG. 6 illustrates the use of pressure to effect the automatic depth reading by means of pressure load cell 50, other means may be used. For example, the pivotal movement of neck 42 can result in causing an electrical contact to be made to actuate the automatic depth reading.

FIGS. 7-9 illustrate a more simplified form of this invention, the probe assembly 100 includes a tool 102 having a straight neck portion 104 offset from the handle portion. The probe 106 is detachably mounted in any suitable manner, such as in the prior embodiment. Fiber optics 108 transmit light to probe 106 which in turn is a light conducting disposable plastic element having a scale 110 thereon. For example, probe 106 could be from 12 to 15 millimeters long and the scale could be a mark at each millimeter.

Probe assembly 100 also includes a sensing section 112 which would include a photodiode 114 and a lens 116 with a electrical wiring 118 similar to the previous embodiment.

As shown tool 102 could include a button 120 and an LED 122, similar to button 58 and LED 56. Button 120 could be utilized to actuate photodiode 114 for the taking of the reference and of the depth readings. LED 122 would light when the readings are being taken.

This embodiment would be used in a manner similar to the previous embodiment wherein an initial reading would be taken before probe 106 is inserted into the gum pocket and then a second reading would be taken which would indicate the light corresponding to the amount of probe 106 still extending out of the gum pocket. By the subtractive method the depth of the gum pocket would be determined. A difference from the previous embodiment is that the second or depth reading would be manually taken when the periodontist feels the bottom of the pocket being reached. Although this embodiment relies upon the experience of the periodontist to initiate the second reading, it is more accurate than prior methods which do not use a light transmitting probe. This embodiment would still make use of the computer and its printer.

As should be apparent this invention provides a means for quickly, automatically and reliably providing a reading or determination of the depth of a gum pocket in a manner which overcomes the deficiencies of prior methods which rely upon the manual application of force to determine when the base of the gum pocket is reached and visual observation to measure the depth. It is to be understood that this invention is based upon the recognition that the depth of a gum pocket can be determined by utilizing a light conducting probe wherein the amount of light of the probe can be measured after the probe is inserted into a gum pocket. In a preferred practice of this invention such measurement takes place by comparing the amount of light of the probe under reference conditions before the probe is inserted into the gum pocket with the amount of light after the probe is inserted into the gum pocket. In a more refined form of this invention, utilization is made of known techniques in the computer field to automatically make this comparison by the subtractive light method. Further, known techniques may be used to assure or maximize the reliability of the comparison by taking into account the ambient conditions which might affect the light readings. Because such computer techniques are known to those skilled in the art it is not necessary to describe those techniques in detail herein.

It is to be understood that, although the invention has been described with respect to the measurement of a gum pocket, the invention may be practiced for the other types of measurements such as the depth of any hole.

What is claimed is:

1. A probe assembly for depth measurement comprising a hand held portable tool having a handle section at one end thereof, a probe mounted to the end of said tool remote from said handle, said probe being made of a light conducting material, means for transmitting light to said probe, and means for indicating the depth of a gum pocket or the like in accordance with the length of said probe remaining out of the pocket when said probe is inserted into the pocket.

2. The assembly of claim 1 wherein said indicating means comprises a visible scale on said probe.

3. The assembly of claim 1 wherein said indicating means includes means for measuring the amount of light of said probe just before and just after said probe is inserted into the pocket.

4. The assembly of claim 3 wherein said means for transmitting light includes fiber optics associated with said probe.

5. The assembly of claim 4 wherein said indicating means includes a photodiode and lens having a field of view corresponding to the length of said probe.

6. The assembly of claim 5 wherein said tool includes a neck section pivotally mounted to said handle, said probe being secured to said neck section whereby said neck section pivots upon said probe reaching the base of the pocket, actuating means for actuating said indicating means, and an actuating member on said neck section for activating said actuating means upon pivotal movement of said neck section.

7. The assembly of claim 6 wherein said actuating means comprises a sensor disposed in contact with one end of an adjustable resistance member.

8. The assembly of claim 7 wherein said actuating member comprises a sleeve resiliently mounted to said neck section, and said sensor being mounted to said sleeve.

9. The assembly of claim 8 including a manual button for actuating said indicating means to take a reference reading before said probe is inserted in the pocket.

10. The assembly of claim 9 including a computer and printer means for calibrating the depth of the pocket in accordance with information provided by said indicating means and for providing a record of the depth.

11. The assembly of claim 10 wherein said probe is detachably mounted to said neck section.

12. The assembly of claim 11 wherein said probe includes a visible scale.

13. The assembly of claim 12 wherein said fiber optic transmits light to said probe by means of a lens and mirror assembly.

14. The assembly of claim 4 wherein said fiber optics transmits light to said probe by means of a lens and mirror assembly.

15. The assembly of claim 1 wherein said probe is a dental probe detachably mounted to said neck section.

16. A method of determining the depth of a pocket comprising transmitting light to a light conducting probe, providing a reference reading by measuring the light over a field of the full length of the probe, inserting the probe into the pocket, measuring the light over the portion of the probe remaining out of the pocket to obtain a second reading, and comparing the reference reading with the second reading to determine the pocket depth.

17. The method of claim 16 wherein the pocket is a gum pocket.

* * * * *